United States Patent [19]

Baker et al.

[11] 4,060,000  
[45] Nov. 29, 1977

[54] LADING SAMPLING DEVICE FOR A TANK

[75] Inventors: Forrest L. Baker, St. Charles; Gunter R. Behle, St. Peters, both of Mo.

[73] Assignee: ACF Industries, Incorporated, New York, N.Y.

[21] Appl. No.: 700,107

[22] Filed: June 28, 1976

[51] Int. Cl.² .............................................. G01N 1/16
[52] U.S. Cl. ................................................ 73/421 B
[58] Field of Search .............. 73/421 B, 424, 425.4 R, 73/422 R, 298

[56] References Cited

U.S. PATENT DOCUMENTS

| | | | |
|---|---|---|---|
| 2,158,803 | 5/1939 | Renfro | 73/421 B |
| 2,377,343 | 6/1945 | Holicer | 73/298 |
| 2,702,475 | 2/1955 | Dougherty et al. | 73/421 B |
| 3,024,660 | 3/1962 | Tothill | 73/424 |

*Primary Examiner*—James J. Gill  
*Assistant Examiner*—Anthony V. Ciarlante  
*Attorney, Agent, or Firm*—Henry W. Cummings

[57] ABSTRACT

A lading sampling device for a tank includes two concentric, telescoped tubes extending upwardly within the tank. The tubes are mounted for axial rotation relatively to each other and each tube has a plurality of vertically spaced openings through the wall thereof through which a lading sample may pass from the tank into the innermost tube when the openings in the two tubes are aligned. The relative circumferential spacing of the openings in the two tubes is such that only openings at the same level in each tube are aligned to receive a lading sample in a particular rotated position of the tubes whereby samples of lading may be selectively taken at different levels in the tank by relative rotation of the tubes a seal is placed between the inner and the outer tube between each level of vertically spaced openings. In one embodiment, the tubes are assembled in short pieces to facilitate retrofitting existing tanks with the sampling device where limited clearance exists below the bottom of the tank.

23 Claims, 13 Drawing Figures

LOWER PORTION

UPPER PORTION

LOWER PORTION

UPPER PORTION

LADING SAMPLING DEVICE FOR A TANK

BACKGROUND OF THE INVENTION

This invention relates to a lading sampling device. In particular, it relates to a lading sampling device for taking a sample of the lading at a given level in the tank only. Thus the composition of the lading at various levels in the tank can be analyzed and compared to samples taken from other levels.

One common lading sampling technique is to rely on pressure in the tank which exceeds the atmospheric pressure to force a sample out. For example, as described in U.S. Pat. No. 1,669,776, a hollow sampling tube open at the inlet end and closed at the outlet end with a valve or removable plug is lowered to the level in the tank where a sample is desired. The outlet end is opened to the atmosphere and the pressure in the tank above atmospheric forces the sample from the given level out of the tank.

U.S. Pat. No. 1,739,731 discloses a pair of concentric sampling tubes including an outer guide tube containing perforations throughout its length. A sampling tube without perforations is lowered longitudinally within the guide tube to obtain a vertical core sample of all levels in the tank. On page 1, col. 1, this patent refers to prior use of telescoped, relatively rotatable tubes provided with perforations in each tube at various levels adapted to register for admission of a sample and to be moved out of registry to trap the sample. There is no indication that the openings located at any one level were circumferentially spaced from the openings at other levels in either of the tubes. Thus, apparently this prior technique was directed to taking a sample from all levels in the tank rather than to taking a sample from a selected level only.

SUMMARY OF THE INVENTION

A lading sampling device for a tank includes two concentric, telescoped tubes extending upwardly within the tank. The tubes are mounted for axial rotation relatively to each other and each tube has a plurality of vertically spaced openings through the wall thereof through which a lading sample may pass from the tank into the innermost tube when the openings in the two tubes are aligned. The relative circumferential spacing of the openings in the two tubes is such that only openings at the same level in each tube are aligned to receive a lading sample in a particular rotated position of the tubes whereby samples of lading may be selectively taken at different levels in the tank by relative rotation of the tubes. In one embodiment the outer tube is fixed and the inner tube is rotatable. In order to avoid leakage from level to level, the various sampling levels may be sealed with respect to each other. The inner tube includes a lower portion extending below the outer tube. A handle to rotate the inner tube is attached to the lower portion of the inner tube. A sample of the lading may be taken at any given level in the tank by rotation of the inner tube to obtain alignment of the inner sampling openings with the outer sampling openings at the desired level. Preferably indexing means are provided to facilitate alignment of the openings in the respective tubes at various levels where a sample may be taken. A mounting plate is attached to the bottom opening in the tank and the concentric tubes are attached to a sampling opening in the mounting plate. In one embodiment the lower surface of the mounting plate contains indexing openings which correspond to the circumferential portions of the inner tube in which the inner sampling openings align with the outer sampling openings at various levels. A ratchet may be mounted on the lower portion of the inner tube. The ratchet includes spring biased pawls which enter the indexing openings in the mounting plate to maintain the inner tube fixed in the proper sampling position to take a sample at a given level in tank. In one embodiment individual inner and outer sampling tubes are concentrically mounted in the bottom opening in the tank. In another embodiment the inner and outer sampling tubes are inserted into the bottom opening in short pieces and assembled in the tank to facilitate retrofitting existing tanks.

THE DRAWINGS

DESCRIPTION OF PREFERRED EMBODIMENTS

Figure 1:
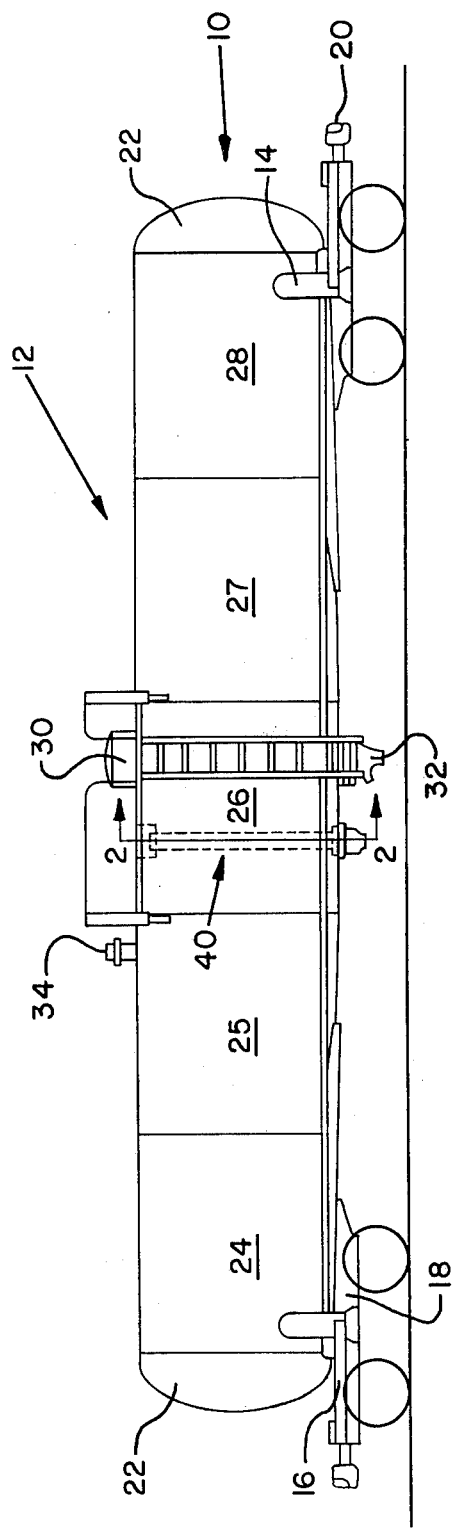
FIG. 1 is a side elevation view of a railway tank car in which the lading sampling device of the present invention may be mounted.

The sampling device of the present invention may be utilized with an overland tank truck, an intermodal tank container or container mounted on a ship. However, by way of example, the sampling device of the present invention will be described and illustrated in connection with its application to a railway tank car.

In the drawings, a railway tank car 10 is illustrated in which a tank 12 is mounted upon cradles 14 which are supported by stub sills 16 and trucks 18 at opposite ends of the car. A conventional coupler 20 and a draft gear (not shown) are mounted within the stub sills. The tank includes end portions 22 and tank sections 24, 25, 26, 27 and 28 welded together to form an integral tank.

The tank car may be loaded through a manway 30 of conventional construction and may be loaded and/or unloaded through a bottom operated unloading valve 32, for example, according to the teachings of one or more U.S. Pat. Nos. 3,591,131 or 3,661,355 or 3,721,424 or 3,227,101 or according to the teachings of application Ser. No. 513,082 filed Oct. 10, 1974, assigned to the same assignee as the present application. A pressure relief valve 34 may be provided of conventional construction whereby the pressure in the tank will be vented to avoid the tank bursting and endangering life and property adjacent the railroad. An example of a suitable relief valve is described in U.S. Pat. No. 3,845,876.

Figure 2:
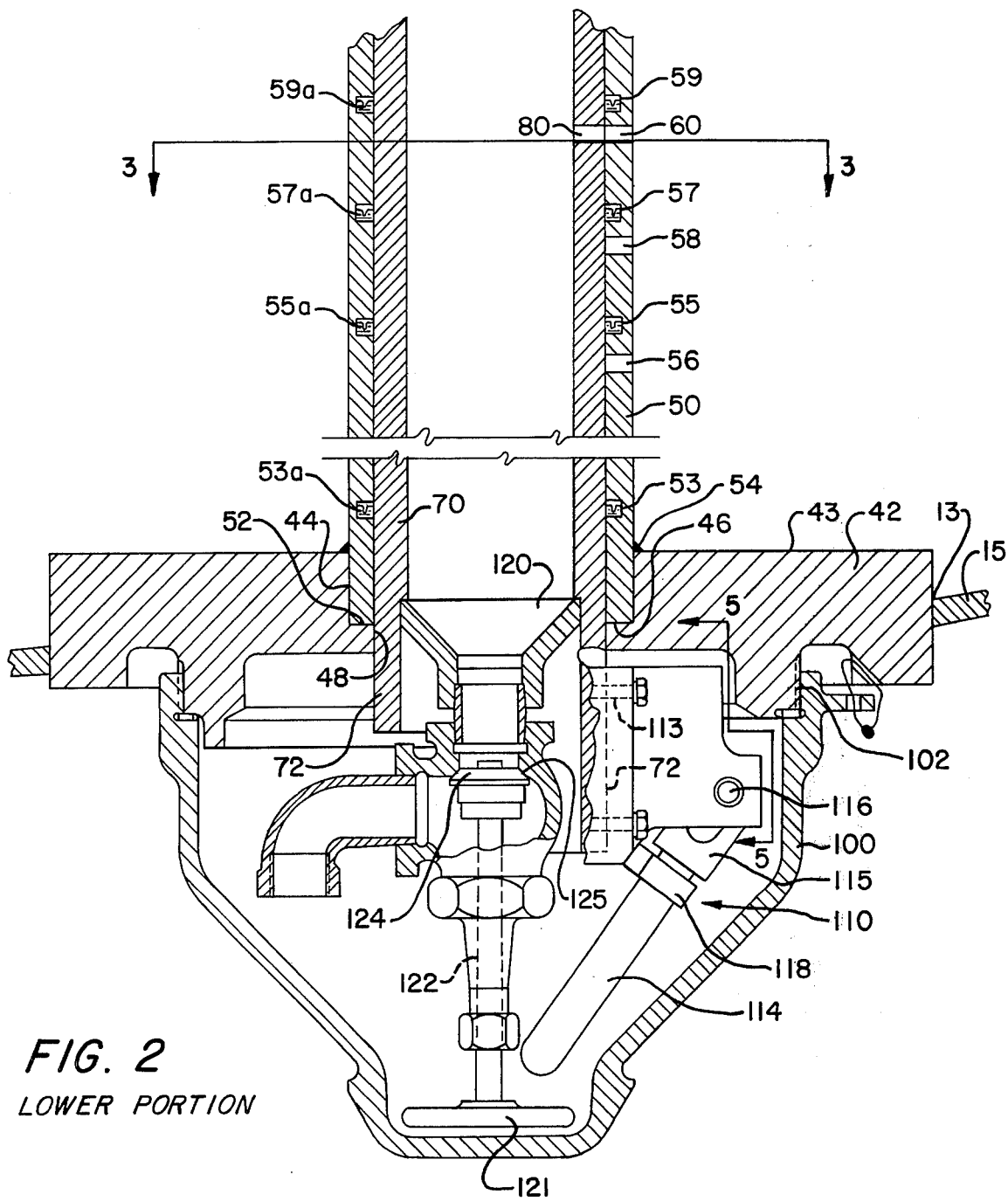
FIG. 2 is a sectional view looking in the direction of the arrows along the line 2—2 in FIG. 1 illustrating the lower portion of the lading sampling device of the present invention mounted in a railway tank car.

In accordance with the present invention a lading sampling device 40 is provided. As shown in FIG. 2 the sampling device is mounted in a bottom opening 13 in the tank bottom 15. The sampling device includes a mounting plate 42 mounted within bottom opening 13 in tank bottom 15. Mounting plate 42 in turn has a sampling opening therein 44 which defines a shoulder 46 and includes a portion of reduced diameter 48.

An outer sampling tube 50 is attached by mechanical fasteners or welding to mounting plate 42 with the bottom 52 of tube 50 resting upon shoulder 46. Tube 50 may be welded as indicated at 54 to the upper surface 43 of mounting plate 42. Tube 50 extends upwardly into the tank and includes a plurality of vertically spaced sampling openings 56, 58, 60 and 62 formed through the wall thereof. The number of openings provided in tube 50 and the vertical placement of these openings depends upon where it is desired to take a sample of the lading in the tank. The openings are provided in the tube at whatever level(s) it is desired to take a sample of the lading from the tank. The sampling openings 56, 58, 60 and 62 are preferably vertically aligned.

Figure 3:
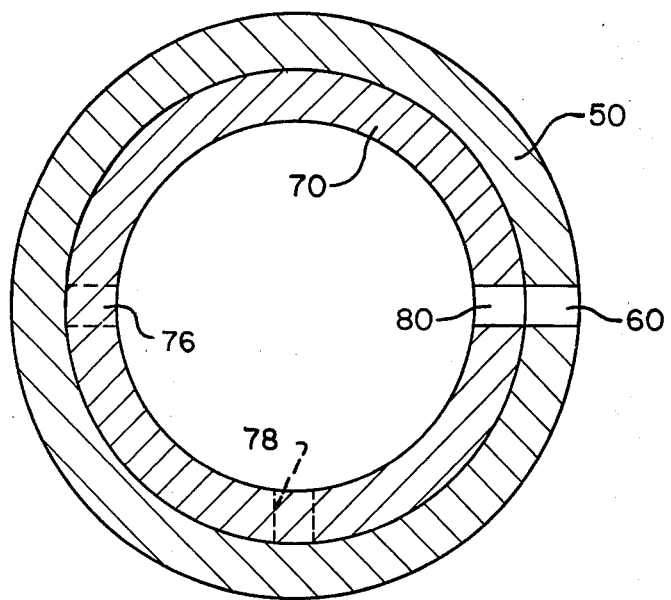
FIG. 3 is a sectional view looking in the direction of the arrows along the line 3—3 in FIG. 2.
Figure 4:
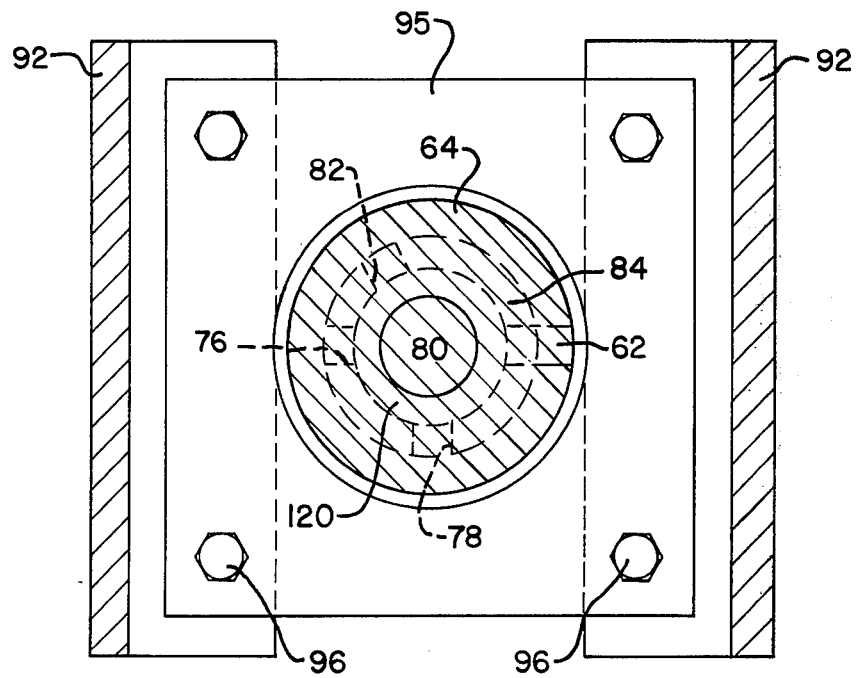
FIG. 4 is a sectional view looking in the direction of the arrows along the line 4—4 in FIG. 2A.

Mounted concentrically within tube 50 is a rotatable inner sampling tube 70. Tube 70 includes a lower portion 72 which extends below the bottom 52 of fixed tube 50 and through the portion of reduced diameter 48 in mounting plate 42. Inner sampling openings 76, 78, 80 and 82 are provided in tube 70 at the same level respectively as outer sampling openings 56, 58, 60 and 62 in the outer fixed tube. However, as is apparent from FIGS. 3 and 4, the inner sampling openings 76, 78, 80 and 82 are circumferentially spaced in the inner tube 70 in contrast to the vertically aligned outer sampling openings 56, 58, 60 and 62 in the outer fixed tube 50. As is discussed in more detail hereafter, with this arrangement or openings in the outer and inner tubes 50 and 70, only the openings in the tubes 50 and 70 which are at the same level will be aligned to receive a sample from the tank when the tube 70 is in a particular rotated position relative to tube 50.

Grooves 53 may be provided in outer fixed member 50 and a suitable O-ring seal member 53a inserted therein. If desired, additional grooves 55, 57 and 59 may be provided each having seals 55a, 57a, and 59a to seal the inner tube with respect to the outer tube at each level of outer sampling openings with respect to the inner sampling openings.

Figure 2A:
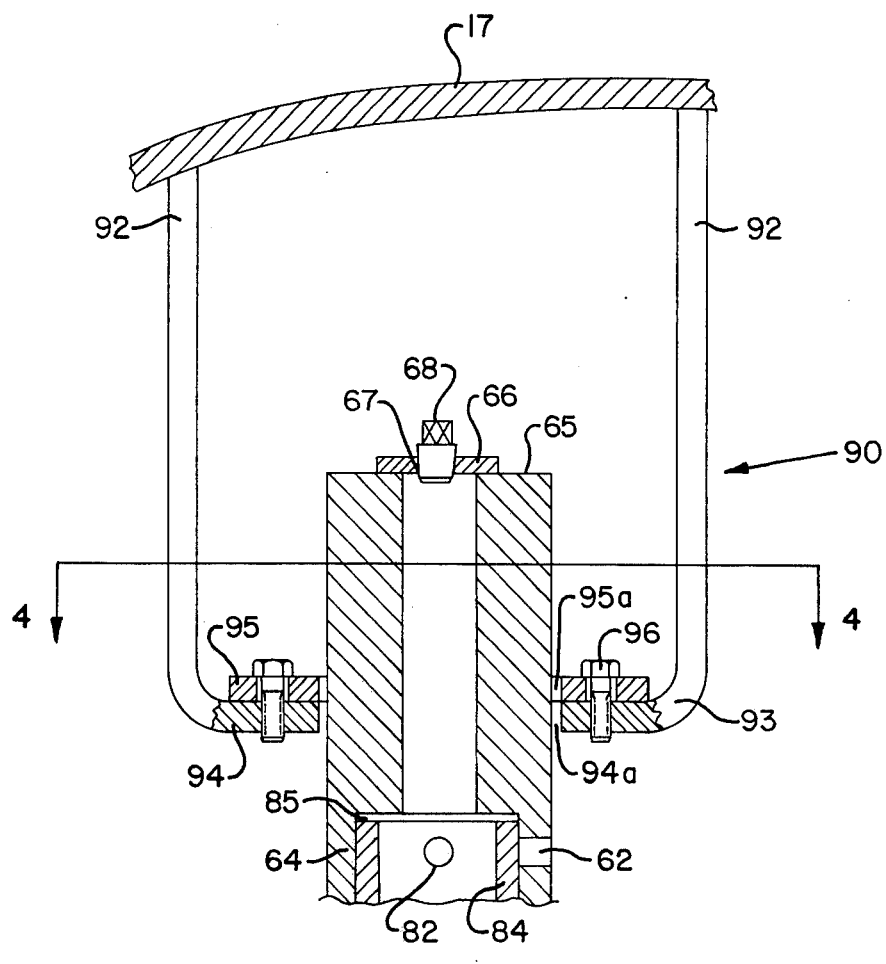
FIG. 2A is a view similar to FIG. 2 illustrating the upper portion of the sampling device and the bracket assembly for maintaining the sampling device from moving longitudinally in the tank.

The upper portion 84 of the inner tube 70 terminates (FIG. 2A) adjacent an upper portion 64 of the outer tube 50 which is of reduced inner diameter. Clearance provided at 85 allows for longitudinal expansion of the inner tube 70. Outer tube upper portion 64 extends upwardly into a bracket assembly 90. Bracket assembly 90 includes a pair of bracket members 92 attached to the roof 17 of the tank 12, for example, by welding. The bracket members depend vertically from the tank roof and are bent at 93 to include a generally horizontal portion 94. A plate 95 is attached to horizontal bracket portions 94 with fasteners 96. Horizontal portion 94 and plate 95 have openings therein 94a and 95a through which outer tube upper portion 64 extends with clearance 94a and 95a. Bracket assembly 90 maintains the concentric tubes in place when longitudinal loads, such as impacts, are applied to the car. For example, such longitudinal impacts may result in lading movement longitudinally in the car which would in turn tend to move the sampling device longitudinally in the car. The bracket assembly 90 prevents this movement. The clearance 94a, 95a between outer upper portion 64, and horizontal portion 94 and plate 95 allows expansion and contraction of outer tube 70. A plate 66 is attached to the upper surfaces 65 of outer tube upper portion 64 and removable plug 68 is inserted in an opening 67 in plate 66. Plug 68 prevents lading from entering the sampling tubes when the car is full or nearly full. If plug 68 is removed the sampling tubes can function as a full tank indicator or as an emergency overflow drain.

Figure 6:
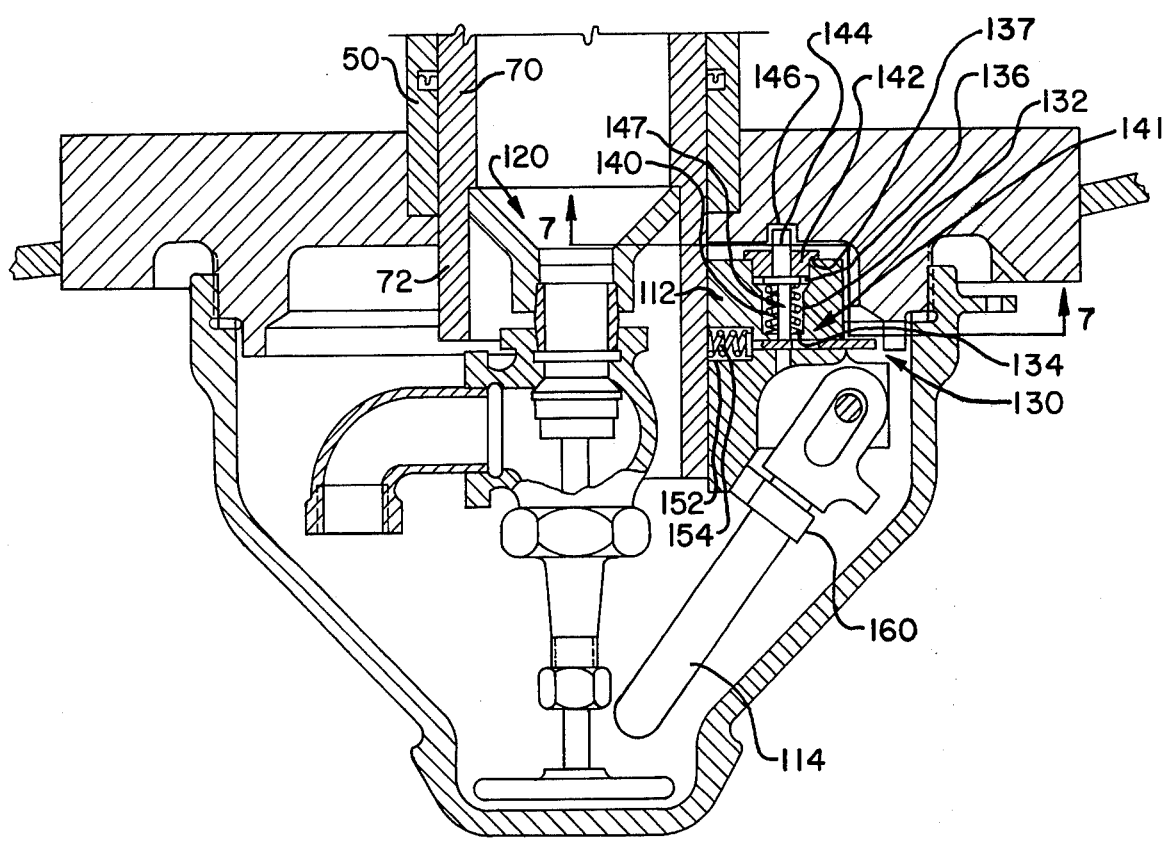
FIG. 6 is an enlarged sectional view of the lower portion of FIG. 2 illustrating the ratchet device for rotating the inner tube in accordance with the present invention.

At the bottom of the sampling device a removable cap 100 is provided which engages a threaded shoulder 102 provided on mounting plate 42. A handle assembly 110 is provided to rotate inner tube 70 relative to outer tube 50. This assembly includes a base portion 112 attached to the lower portion 72 of inner tube 70 by fasteners 113 (FIG. 6). A handle 114 is attached to base portion lugs 115 by means of pivot pin 116. A handle lock 118 mounted on base portion 112 holds handle 114 in place when cap 100 is in place engaging threads 103 on shoulder 102.

A funnel 120 is provided within the lower end of the inner tube 70 having a depending portion 125 and a valve 121 is secured to portion 125 for removing the sample. Valve 121 includes a valve stem 122 having a valve plug thereon 124. Rotation of handle 121 in one direction will move valve plug 124 from valve seat 125 to remove the sample. Rotation of valve 121 in the opposite direction will return valve plug 124 to a closed position on valve seat 125.

To operate the sampling device, the cap 100 is removed, handle 114 is pivoted about pin 116 into the horizontal position and inner tube 70 rotated relative to fixed tube 50 by handle 114. The sampling openings in the inner tube 70 are circumferentially spaced such that rotation of inner tube 70 in one direction will result first in alignment of opening 62 and outer opening 82 located highest in the tank and a sample from the tank at this level will pass through the aligned openings into tube 70 and pass to the bottom of tube 70. Further rotation of tube 70 in the same direction will result in alignment of inner opening 60 and outer opening 80 located next highest in the tank whereby a sample at this level may pass into the inner tube 70. Friction between inner tube 70 and outer tube 50 will maintain the tubes in proper relative position while a sample is taken. Samples may be taken consecutively from the highest level to the lowest level or to the lowest level to the highest level as desired by appropriate rotation of inner tube 70. The sample may be stored at the bottom of the inner tube.

Figure 5:
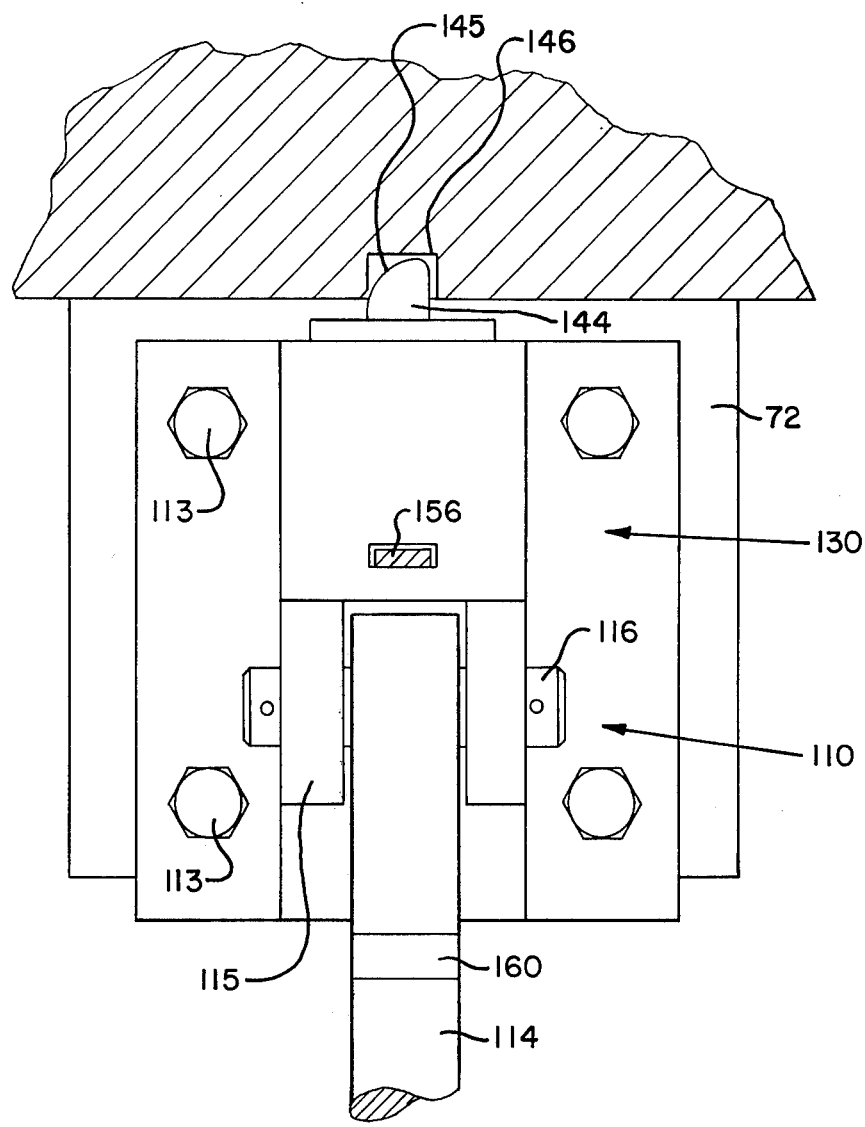
FIG. 5 is a sectional view looking in the direction of the arrows along the line 5—5 in FIG. 2.
Figure 7:
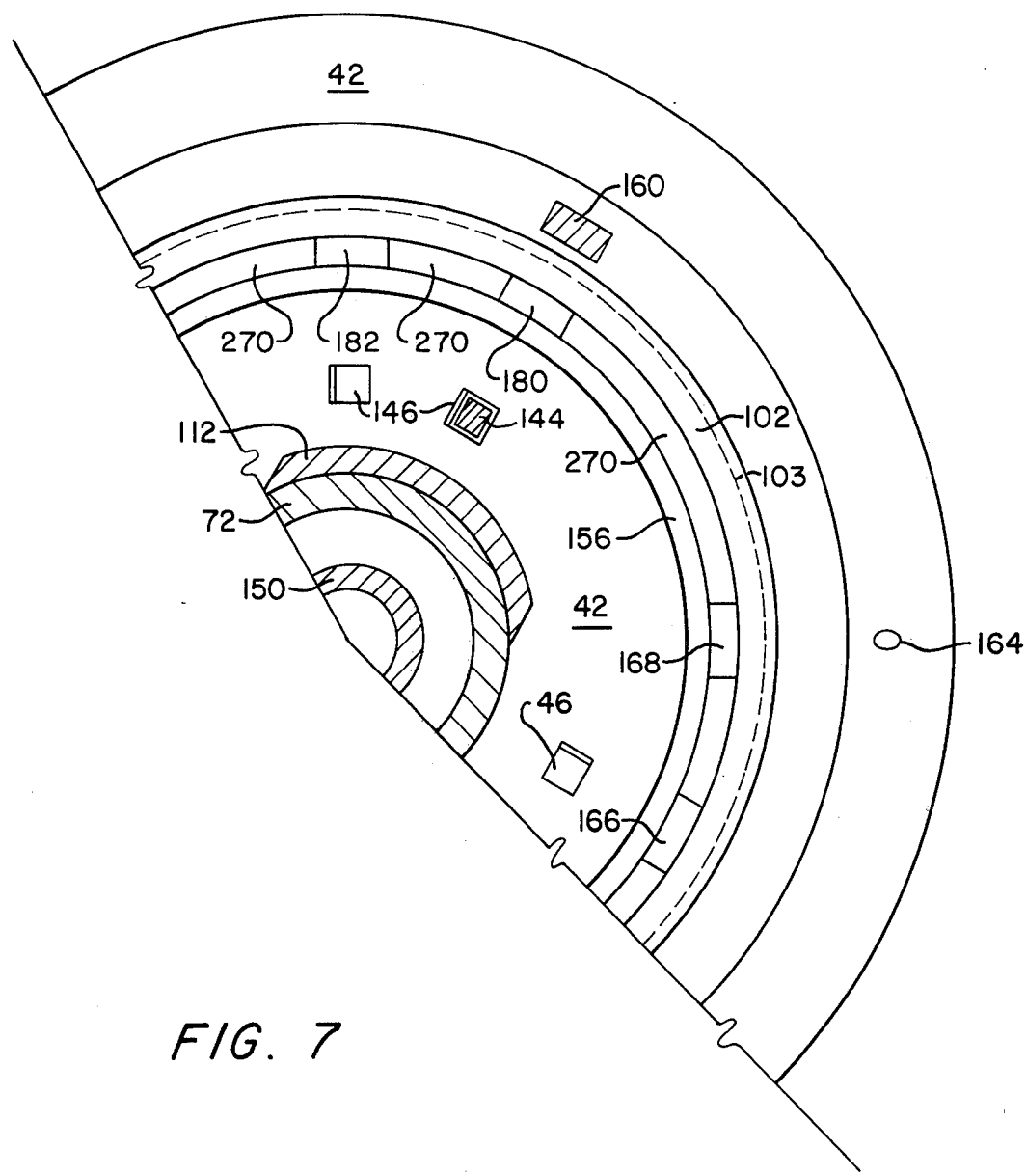
FIG. 7 is a sectional view looking in the direction of the arrows along the line 7—7 in FIG. 6 with the cap removed for clarity.

In order to facilitate obtaining alignment of the inner and outer openings at the level where it is desired to take a sample, a ratchet device 130 is attached to lower portion 72 of rotatable inner member 70. As shown best in FIG. 6, this ratchet device 130 includes a vertical bore 132 provided in the base plate 112. The bore 132 includes a pair of shoulders 134 and 136. A compressive spring 140 is received in bore 132 and is seated upon shoulder 134. A locking pawl 141 is slidably received in the bore 132 and a guide 142 which engages shoulder 136 and upper surface 137 of base portion 112 is secured in the bore 132 and retains the pawl 141 in the bore 132. Locking pawl 141 includes a vertically extending locking end 144 which extends through the guide 142 and a depending pin portion 147 which extends down through spring 140. A plurality of indexing openings 146 (FIG. 7) are provided in the lower surface of mounting plate 42. Openings 146 correspond to the positions in which the openings in the inner tube 70 align with respective openings in the outer tube 50. As shown in FIG. 5, locking end 144 of the pawl 141 has a camming contour 145 at the outer end which is adapted to engage within the indexing openings 146. A horizontal slot 152 formed in the base 112 has a spring 154 mounted therein which urges a horizontal plate 156 outwardly. Pin 147 of the pawl 141 engages the upper surface of the plate 156, maintaining the pawl 141 in the extended, locked position. Plate 156 includes an opening 158 and when handle 114 is swung into the horizontal position, a handle lug 160 engages the end of plate 156 and moves plate 156 radially inwardly against the bias of spring 154 until the opening 158 aligns with the pin portion 147 of the pawl 141 whereby the pawl 141 may move downwardly against the force of spring 140. Until this occurs, locking end 144 of the pawl 141 cannot be removed from the openings 146 because the pin 147 of pawl 141 is resting on the upper surface 157 of plate 156. Rotation of handle 114 in the horizontal position results in the cam surface 145 forcing the locking end 144 of the pawl 141 out of the openings 146 against the bias of spring 140. As the ratchet assembly 130 is rotated further, the locking end 144 of the pawl 141 rides along against the lower surface of mounting plate 42 until the next opening 146 is reached, at which point the bias of spring 140 will move the locking end 144 into the opening and will hold the ratchet assembly in this new sampling position. In this new sampling position one of the openings in the inner tube 70 will align with openings in the outer tube so that a sample may be taken. Further rotation of ratchet assembly 130 will result in alignment of inner openings and outer openings at other desired sampling levels. A car seal 161 may be inserted through an opening 162 in cap 100 and an opening 164 in mounting plate 42. Slots 166, 168, 180, and 182 may be provided at spaced locations around the circumference of shoulder 102 which align with the sampling positions where pawl 141 aligns with openings 146. This solid portion 270 of shoulder 102 prevents the operator from moving handle 110 inwardly except at sampling positions.

The embodiment shown in FIGS. 1-6 of the drawings is satisfactory when sufficient clearance exists below the tank to insert the tubes 50 and 70. Thus tubes 50 and 70 are readily inserted into new tanks or tanks which are being repaired and overhauled and can be rotated to a position where clearance below the opening in the bottom of the tank is not a problem.

However, it often occurs that it is desired to insert a sampling device into a tank in which there is limited clearance below the tank, for example, a tank which is operating in the field. It is often inconvenient in the field to lift the tank up and rotate it so that long tubes can be readily inserted into the opening in the bottom of the tank.

In the embodiment shown in FIGS. 8-11 the inner and outer tubes are assembled from short sections which are readily inserted into a tank having limited clearance below the opening in the bottom of the tank. In this embodiment a mounting plate 42 is again provided with a shoulder 46 and a portion of reduced diameter 48. A fixed outer tube 250 includes an outer tube base portion 252 which engages shoulder 46 and is welded to upper surface 43. An inner rotatable tube 370 includes an inner tube base portion 372 having a depending lower portion 374 upon which handle assembly 110 and ratchet assembly 130, described above, may be mounted. A groove 252a is provided into which is inserted a seal 252b. Inner tube base portion 372 includes an inward extension 376 which defines a shoulder 376 and an upper extension 379 which includes openings 380. A thrust washer 256 is inserted on flange 253. Pins 382 are inserted part way into openings 380, and inner tube base portion 372 with handle assembly 110 and ratchet assembly 130 in place is inserted upwardly within outer tube base portion adapter 300. Outer tube section member 310 includes a lower flange portion 312 and an upper flange portion 314. Lading sampling openings 315 in outer tube section member 310 are provided at the same level as lading openings 304 in base adapter 300. Fasteners 313 may be inserted through flanges 312 and 253 to engage outer tube base portion 252. This completes assembly of a base portion subassembly labeled B in FIG. 8.

Figure 9:
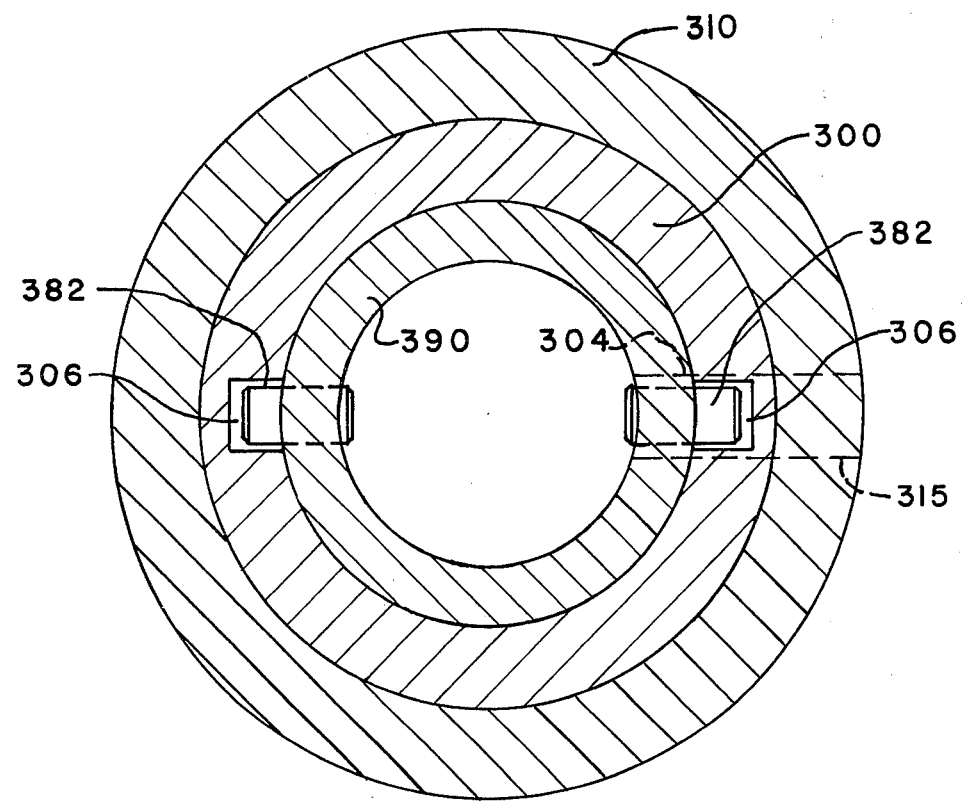
FIG. 9 is a sectional view looking in the direction of the arrows along the line 9—9 in FIG. 8.
Figure 10:
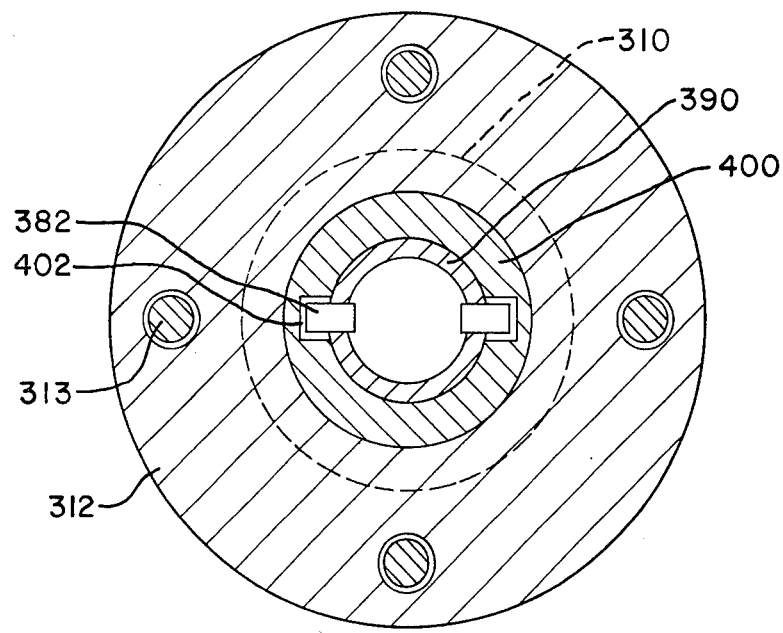
FIG. 10 is a sectional view looking in the direction of the arrows along the line 10—10 in FIG. 8.

After fasteners 313 are tightened in place an inner tube section member 390 is inserted within outer tube section member 310. Inner tube section member 390 includes lower openings 392 and upper openings 394 each containing pins 382. As shown in FIG. 9 pins 382 are placed within slots 306 of base portion adapter 300 and are rotatable therewith. Next another thrust washer 256 is applied in the groove 314a within flange portion 314. Flange portion 314 further includes groove 314b having mounted therein an O-ring seal 314c.

Next an inner tube main body adapter 400 having lower slots 402 (FIG. 10) and upper slots 404 (FIG. 11) is provided. Lower slots 402 surround pins 382 located in openings 394 in inner tube main body subsection member 390 and are rotatable therewith. Inner tube main body adapter further includes a lading opening 406.

Next another outer tube section member 310 is applied concentrically around main body adapter 400. Outer tube section member 310 includes a lower flange portion 312 and an upper flange portion 314. Openings 315 are again provided at the same level as openings 406 in the inner tube main body adapter. Fasteners 313 hold the abutting main-body flanges 312 and 314 together. This completes a first main body subassembly labeled $S_1$ in the drawings. Additional subassemblies $S_2$, $S_3$ etc. may be similarly installed to obtain any desired height of concentric tubes for lading sampling in the tank. The inner tube main body adapter to be installed at various levels must be selected carefully by the assembler to provide the inner tube circumferentially spaced openings which align with the outer openings as the inner member is rotated.

Figure 8:
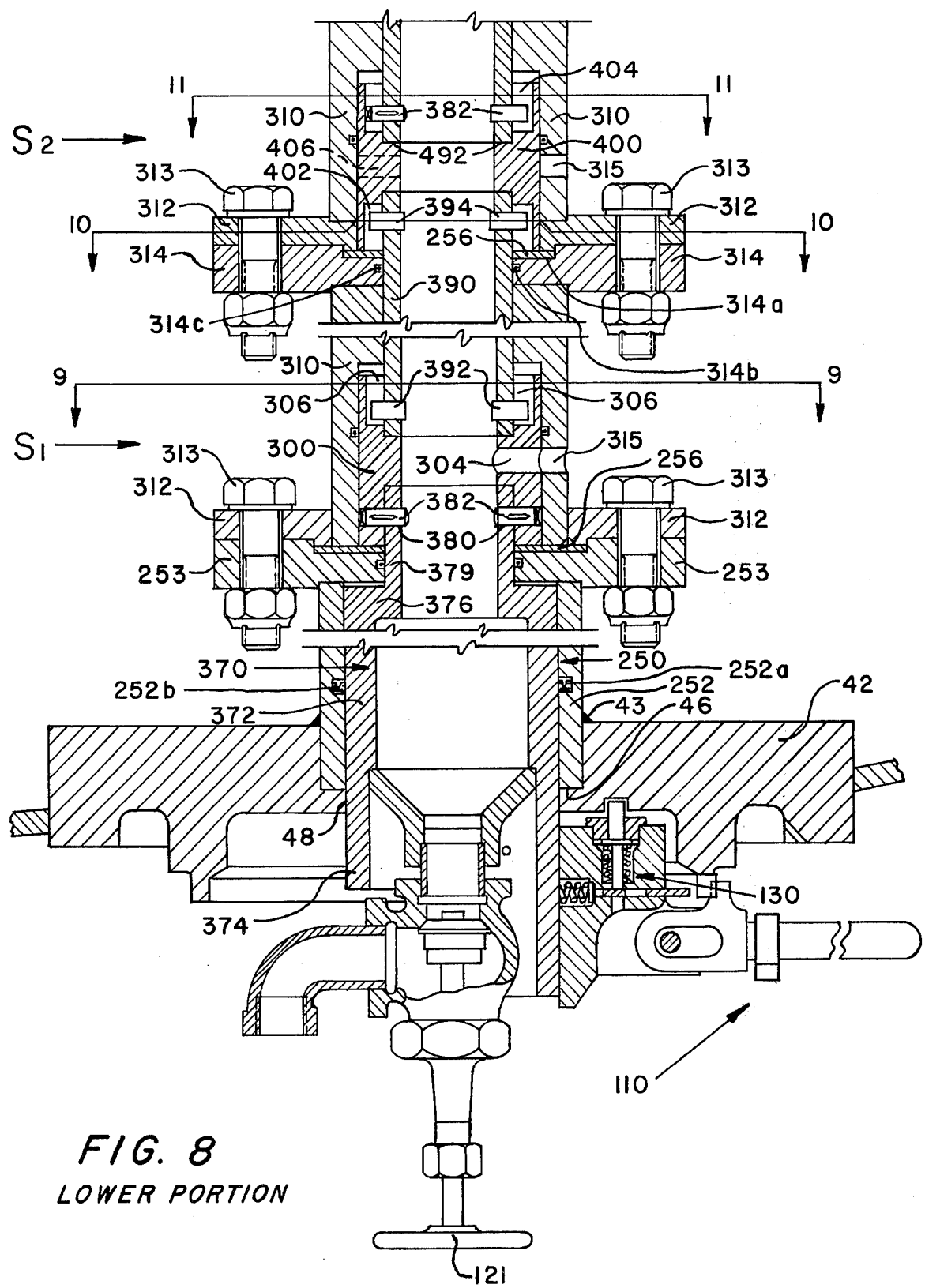
FIG. 8 is a sectional view similar to FIG. 2 illustrating the lower portion of an alternative embodiment of the sampling device of the present invention.
Figure 8A:
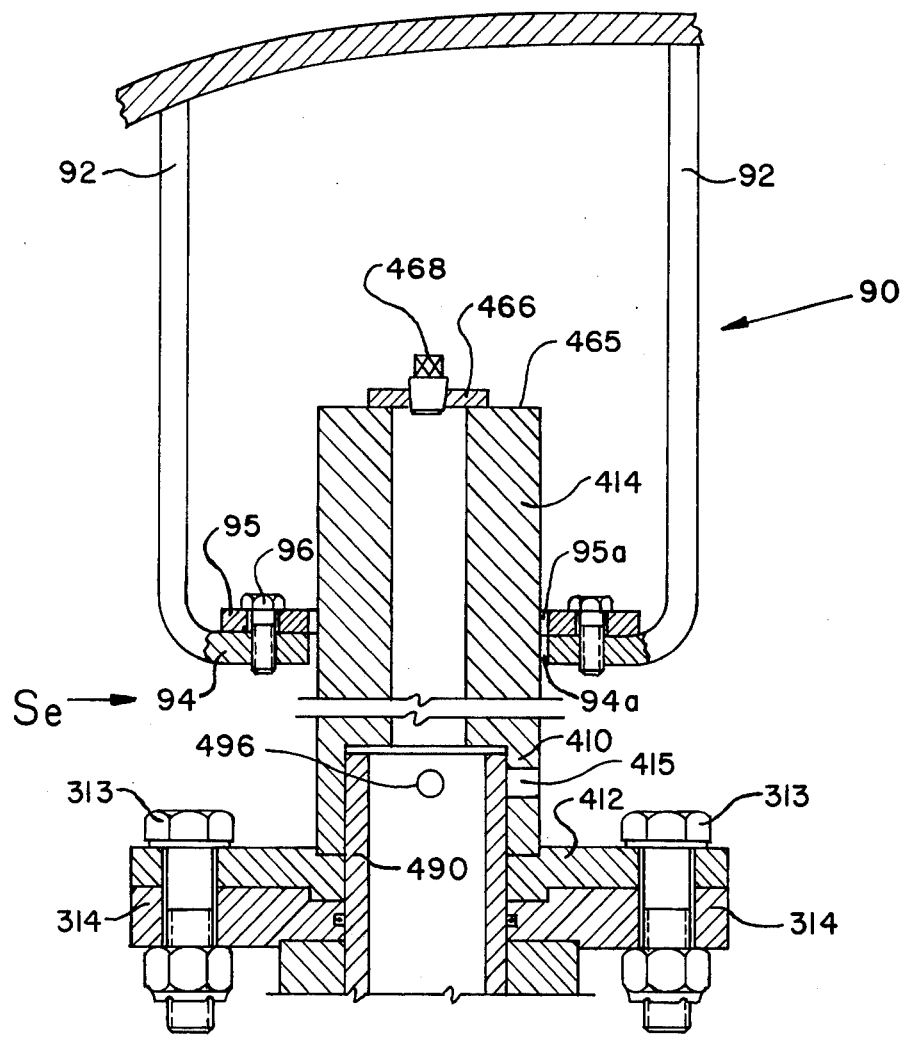
FIG. 8A is a sectional view of the upper portion of the embodiment shown in FIG. 8.
Figure 11:
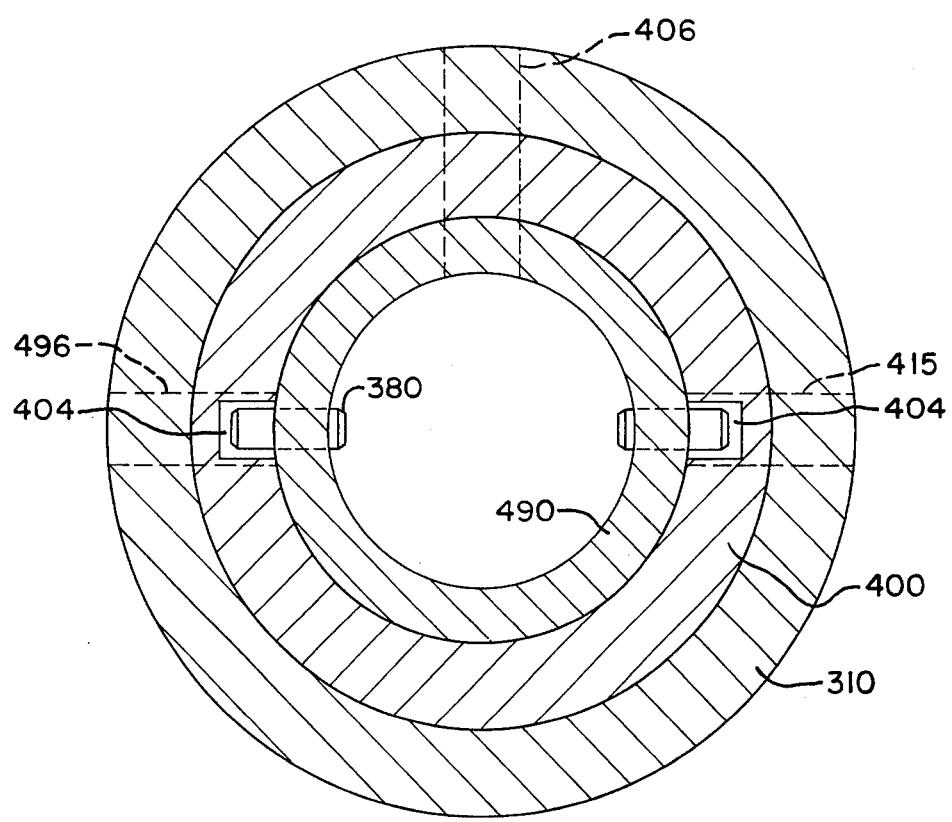
FIG. 11 is a sectional view looking in the direction of the arrows along the line 11—11 in FIG. 8.

The last and highest subsection assembly $S_e$ includes an upper inner tube section member 490 inserted within outer tube section member 310. Upper inner tube section member 490 has lower openings 492 having pins therein 382 which extend within slots 404 in inner tube main body adapter 400 and are rotatable therewith (FIG. 11). In addition, an upper lading sampling opening 496 is provided in upper inner tube section member 490 as shown in FIG. 8A.

An upper outer tube section member 410 is provided having a lower flange portion 412 and a lading sampling opening therein 415. Lading sampling opening 415 is out of register with lading sampling opening 496 in upper inner tube section member 490. Upper outer tube section member 410 includes an upper portion 414 which extends within a bracket assembly 90 including brackets 92 having horizontal portions 94 and a plate 95 each having openings therein 94a and 95a as described in detail in regard to FIGS. 2A and 4. A plate 466 may be provided on the upper surface of subsection member 414 and a removable plug 468 also provided. Fasteners 313 are then inserted through flange portions 314 and 412 to complete the assembly of upper subassembly $S_e$.

It will be apparent that the embodiments shown in FIGS. 8 through 11 of the drawings can be assembled in a tank having limited clearance, such as several feet, below the bottom opening in the tank since none of the subsection members exceed this clearance distance. It has particular application to installing the sampling device into existing railway tank cars while they are on the track and do not have to be lifted and rotated to insert long sampling tubes into the bottom opening. It will also be apparent to those skilled in the art that the subsection embodiment shown in FIGS. 8 through 11 may also be utilized to retrofit the sampling device into a wide variety of existing tanks.

Once assembled, the operation of the embodiment shown in FIGS. 8 through 11 is the same as the operation of the embodiment shown in FIGS. 1 through 7.

What is claimed is:

1. A lading sampling device for taking a sample from a given level in a tank comprising:
    two concentric tubes including an inner tube and an outer tube mounted in an opening in the bottom of the tank and extending upwardly inside the tank; means mounting said inner tube for axial rotation relative to said outer tube; a plurality of vertically spaced sample receiving openings formed through the wall of each tube through which a lading sample may pass from the tank into the innermost tube when the respective openings in said two tubes are aligned; the sample receiving openings of one tube being spaced circumferentially relative to the sample receiving openings of the other tube such that only the sample receiving openings at the same level in each tube are aligned to receive a lading sample in a particular rotated position of said tube; sealing means provided between the inner and outer tubes between each sampling level to seal the outer tube relative to the inner tube between the various sampling levels; whereby samples of lading may be selectively taken at different levels in the tank by rotation of the inner tube relative to the outer tube; and means for effecting rotation of said inner tube relative to said outer tube.

2. A lading sampling device for taking a lading sample from one of several preselected horizontal levels in a tank comprising:
    a pair of concentric sampling tubes including an inner tube and an outer tube mounted in a bottom opening in the bottom of the tank and extending upwardly inside the tank; means mounting said inner tube for rotational movement relative to the outer tube; said outer tube having a plurality of vertically spaced outer sample openings therein corresponding to the levels in the tank at which it is desired to take samples; said inner tube having a plurality of vertically spaced inner sampling openings at the same horizontal level as the outer sampling openings, but staggered circumferentially with respect to the outer tube sampling openings so that only one pair of inner and outer sampling openings are in axial alignment and registry at any one time; sealing means provided between the inner and outer tubes between each sampling level to seal the outer tube relative to the inner tube between the various sampling levels; and means to rotate said inner tube relative to the outer tube to align the pair of inner and outer sampling openings at the preselected level.

3. A lading sampling device as set forth in claim 2 wherein position indicating means are attached to the rotatable tube, said position indicating means having a plurality of positions thereon corresponding to the levels at which the openings are positioned to indicate to an operator when a pair of desired inner and outer openings are in registry at the desired level at which the lading sample is being taken.

4. A lading sampling device according to claim 2 wherein individual inner and outer tubes are mounted concentrically in the opening in the bottom of the tank.

5. A lading sampling device according to claim 2 wherein the inner and outer tubes are assembled in short pieces.

6. A lading sampling device according to claim 2 wherein the outer sampling openings are vertically aligned.

7. A lading sampling device for taking a sample from a given level in a tank comprising:
    two concentric sampling tubes mounted in a bottom opening in the bottom of the tank and extending upwardly inside the tank; said sampling tubes including an outer fixed tube including vertically spaced outer sampling openings at various levels in the tank, an inner tube rotatable relative to the outer tube and including vertically spaced inner sampling openings at the same level as said outer sampling openings; said inner openings at one level being circumferentially spaced from the inner openings at other levels in the tank; sealing means provided between said inner and outer tubes between each sampling level to seal the outer tube relative to the inner tube between the various sampling levels; said inner tube including an inner tube lower portion extending below the outer tube; and means attached to said lower portion to rotate the inner tube relative to the outer tube; whereby a sample of the lading may be taken at any given level in the tank by rotation of the inner tube to obtain alignment of the inner sampling openings with the outer sampling openings at the desired level.

8. A lading sampling device according to claim 6 wherein the outer sampling openings are vertically aligned.

9. A lading sampling device according to claim 7 wherein individual inner and outer tubes are mounted concentrically in the opening in the bottom of the tank.

10. A lading sampling device according to claim 7 wherein the inner and outer tubes are assembled in short pieces.

11. A lading sampling device according to claim 10 wherein a ratchet is mounted on said inner tube lower portion, said ratchet having spring biased pawls and wherein when the inner tube is rotated to a position to take a sample at a given level the spring biased pawl enters an opening in the mounting plate to maintain the inner tube fixed relative to the outer tube while a sample at a given level is taken.

12. A lading sampling device for taking a sample from a given level in a tank comprising:

a pair of concentric tubes mounted in an openings in the bottom of the tank and extending upwardly inside the tank; said tubes including an outer fixed tube including vertically spaced outer sampling openings at various levels in the tank, and an inner tube rotatable relative to the outer tube and including vertically spaced inner sampling openings at the same level as said outer openings; said inner sampling openings at one level being circumferentially spaced from the inner sampling openings at other levels in the tank; sealing means provided between the inner and outer tubes between each sampling level to seal the outer tube relative to the inner tube between the various sampling levels; said inner tube including an inner tube lower portion extending below said outer tube; rotating means attached to said lower portion to rotate the inner tube relative to the outer tube; indexing means attached to said lower portion to maintain alignment of the openings in the inner and outer tubes while a sample is being taken; whereby a sample of the laiding may be taken at any given level in the tank by rotation of the inner tube to obtain alignment of the inner sampling openings with the outer sampling openings at the desired level, and whereby when the inner tube is rotated to a position to take a sample at a given level the indexing means maintains the inner tube fixed relative to the outer tube while a sample at a given level is taken.

13. A lading sampling device according to claim 12 wherein a mounting plate is attached to the bottom opening in the tank and the concentric tubes are attached to a sampling opening in the mounting plate.

14. A lading sampling device according to claim 13 wherein the lower surface of the mounting plate contains indexing openings which correspond to the circumferential positions of the inner tube at which the inner openings align with the outer openings at various levels.

15. A lading sampling device for taking a sample from a given level in a tank comprising:

two concentric sampling tubes mounted in a bottom opening in the bottom of the tank and extending upwardly inside the tank; said tubes including an outer fixed tube including vertically spaced outer sampling openings at various levels in the tank; an inner tube rotatable relative to the outer tube and including vertically spaced inner sampling openings at the same level as said outer openings, said inner openings at one level being circumferentially spaced from the inner openings at other levels in the tank; sealing means provided between the inner and outer tubes between each sampling level to seal the outer tube relative to the inner tube between the various sampling levels; said inner tube including an inner tube lower portion extending below the outer tube; means attached to said lower portion to rotate the inner tube relative to the outer tube; whereby a sample of the lading may be taken at any given level in the tank by rotation of the inner tube to obtain alignment of the inner openings with the outer openings at the desired level; said inner and outer tubes each including short sections which can be inserted into tanks having limited clearance below said bottom opening and then assembled within the tank.

16. A lading sampling device according to claim 15 wherein said outer tube includes shorter outer sections having abutting flanges.

17. A lading sampling device according to claim 16 wherein said inner tube includes short sections which are held in place by said outer sections having abutting flanges.

18. A lading sampling device according to claim 17 wherein said inner tube includes adapters which rotatably engage said short inner tube short sections.

19. A lading sampling device according to claim 18 wherein said inner lading sampling openings are provided in said adapters.

20. A lading sampling device according to claim 19 wherein adapter slots are provided in said adapters and wherein pins are provided in said inner tube short sections and wherein said pins rotatably engage said adapter slots.

21. A lading sampling device according to claim 18 wherein said sampling device includes a mounting plate mounted in said bottom opening and wherein an outer tube base portion engages said mounting plate.

22. A lading sampling device according to claim 16 wherein at least some of said outer tube short sections include a lower flange portion and an upper flange portion, and said lower flange portion and said upper flange portion each respectively engage a flange portion of an adjacent outer section.

23. A lading sampling device for taking a sample from a given level in a tank comprising:

two concentric sampling tubes mounted in a bottom opening in the bottom of the tank and extending upwardly inside the tank; said tubes including an outer fixed tube including vertically spaced outer sampling openings at various levels in the tank, and an inner tube rotatable relative to the outer tube and including vertically spaced inner sampling openings at the same level as said outer openings, said inner openings at one level being circumferentially spaced from the inner openings at other levels in the tank; said inner tube including an inner tube lower portion extending below the outer tube; means attached to said lower portion to rotate the inner tube relative to the outer tube, whereby a sample of the lading may be taken at any given level in the tank by rotation of the inner tube to obtain alignment of the inner sampling openings with the outer sampling openings at the desired level; said sampling tubes each including short sections which can be inserted into tanks having limited clearance below said bottom opening and then assembled within the tank; said outer tube including short outer sections having abutting flanges; said inner tube including short sections which are held in place by said outer sections having abutting flanges, and adapters which rotatably engage said inner tube short section.

* * * * *

UNITED STATES PATENT AND TRADEMARK OFFICE
CERTIFICATE OF CORRECTION

PATENT NO. : 4,060,000
DATED : November 29, 1977
INVENTOR(S) : Forrest L. Baker and Gunter R. Behle It is certified that error appears in the above-identified patent and that said Letters Patent are hereby corrected as shown below:

In the Abstract, line 14, "of the tubes a seal is" should read -- of the tubes. A seal is --.

Column 6, line 17, should read -- an inward extension or shoulder 376 --.

Column 8, claim 8, should be dependent upon claim 7.

Column 9, claim 12, line 34, "laiding" should read -- lading --.

Signed and Sealed this

Twenty-eighth Day of March 1978

[SEAL]

Attest:

RUTH C. MASON
Attesting Officer

LUTRELLE F. PARKER
Acting Commissioner of Patents and Trademarks